(12) United States Patent
Gagnon

(10) Patent No.: US 10,414,794 B2
(45) Date of Patent: Sep. 17, 2019

(54) METHOD OF PURIFYING AN ANTIBODY

(71) Applicant: AGENCY FOR SCIENCE, TECHNOLOGY AND RESEARCH, Singapore (SG)

(72) Inventor: Peter Stanley Gagnon, Singapore (SG)

(73) Assignee: AGENCY FOR SCIENCE, TECHNOLOGY AND RESEARCH, Singapore (SG)

( * ) Notice: Subject to any disclaimer, the term of this patent is extended or adjusted under 35 U.S.C. 154(b) by 319 days.

(21) Appl. No.: 15/120,111

(22) PCT Filed: Feb. 17, 2015

(86) PCT No.: PCT/SG2015/050023
§ 371 (c)(1),
(2) Date: Aug. 18, 2016

(87) PCT Pub. No.: WO2015/126330
PCT Pub. Date: Aug. 27, 2015

(65) Prior Publication Data
US 2017/0057992 A1    Mar. 2, 2017

Related U.S. Application Data

(60) Provisional application No. 61/941,911, filed on Feb. 19, 2014.

(51) Int. Cl.
| | | |
|---|---|---|
| *C07K 1/18* | (2006.01) | |
| *C07K 1/34* | (2006.01) | |
| *C07K 16/06* | (2006.01) | |
| *C07K 1/36* | (2006.01) | |
| *C07K 1/22* | (2006.01) | |
| *C07K 1/30* | (2006.01) | |
| *C07K 16/00* | (2006.01) | |
| *C07K 16/32* | (2006.01) | |

(52) U.S. Cl.
CPC .............. *C07K 1/36* (2013.01); *C07K 1/18* (2013.01); *C07K 1/22* (2013.01); *C07K 1/303* (2013.01); *C07K 1/34* (2013.01); *C07K 16/00* (2013.01); *C07K 16/065* (2013.01); *C07K 16/32* (2013.01)

(58) Field of Classification Search
None
See application file for complete search history.

(56) References Cited

U.S. PATENT DOCUMENTS

| | | | | |
|---|---|---|---|---|
| 8,772,461 B2 * | 7/2014 | Gonzalez | .............. | C07K 1/30 530/412 |
| 2014/0121237 A1 * | 5/2014 | Tripp | .............. | C07D 209/48 514/301 |

FOREIGN PATENT DOCUMENTS

| | | | |
|---|---|---|---|
| WO | WO-0108792 A2 * | 2/2001 | .......... B01D 61/145 |
| WO | WO 2003/102132 | 11/2003 | |
| WO | WO-2008008872 A2 * | 1/2008 | .......... A61L 2/0017 |
| WO | 2013/043608 A1 | 3/2013 | |
| WO | WO2013/180655 A1 | 12/2013 | |
| WO | WO2014/123485 A1 | 8/2014 | |
| WO | WO 2014/133458 | 9/2014 | |
| WO | WO 2014/133459 | 9/2014 | |
| WO | WO 2014/196926 | 12/2014 | |

OTHER PUBLICATIONS

Gagnon, "Purification Tools for Monoclonal Antibodies", Validated Biosystems, 1996, pp. 1-269.
European Patent Office, European Search Report for EP Patent Application No. 18158709.8, dated Jun. 11, 2018, pp. 1-4.
Brown et al., Overloading ion-exchange membranes as a purification step for monoclonal antibodies, Biotechnology and Applied Biochemistry, Jun. 11, 2010, vol. 56(2), pp. 1-12.
Gagnon, Pete, Technology trends in antibody purification, Journal of Chromatography A, Jan. 1, 2012, vol. 1221, pp. 57-70.
Extended European Search Report dated Jul. 28, 2017 for PCT/SG2015050023.
Nian et al., "Void exclusion of antibodies by grafted-ligand porous particle anion exchangers", J. Chromatogr. A, 1282 (2013), pp. 127-132.
International Search Report dated Aug. 24, 2015 for Appln. No. PCT/SG2015/050023.
Chanutin, et al., "The precipitation of Plasma Proteins by Short-Chain Fatty Acids"; Arch. Biochem. Biophys. 89 (1960) pp. 218-220.
Brodsky et al, "Caprylic acid precipitation method for impurity reduction: an alternative to conventional chromatography for monoclonal antibody purification", Biotechnol. Bioeng. 109 (2012) 2589-2598.
Vagenende et al., "Amide-mediated hydrogen bonding at organic crystal/water interfaces enables selective endotoxin binding with picomolar affinity", AACS. Appl. Mater. Interfaces, 22 (2013) pp. 4472-4478.
Borsoi-Ribeiro et al., "Behavior of human immunoglobulin G adsorption onto immobilized Cu(II) affinity hollow-fiber membranes", Journal of Molecular Recognition, Oct. 2013, vol. 26, No. 10, pp. 514-520.
Morais et al, "A model mechanism for protein precipitation by caprylic acid: Application to plasma purification", vol. 59, No. 1, 2012, pp. 50-54.
Van Reis et al., "High-performance tangential flow filtration using charged membranes", Journal of Membrane Science, Jul. 1999, vol. 159, Nos. 1-2, pp. 133-142.

(Continued)

Primary Examiner — Daniel E. Kolker
Assistant Examiner — James L Rogers
(74) Attorney, Agent, or Firm — Pillsbury Winthrop Shaw Pittman, LLP

(57) ABSTRACT

Provided herein is a novel method of purifying an IgG antibody from a preparation by use of an electropositive membrane having a defined porosity.

18 Claims, No Drawings

(56) References Cited

OTHER PUBLICATIONS

Lebreton et al., "Application of High-Performance Tangential Flow Filtration (HPTFF) to the Purification of a Human Pharmaceutical Antibody Fragment expressed in *Escherichia coli*", *Biotechnology and Bioengineering*, Aug. 2008, vol. 100, No. 5, pp. 964-974.

Gan et al., "Characterization and removal of aggregates formed by nonspecific interaction of IgM monoclonal antibodies with chromatin catabolites during cell culture production", *Journal of Chromatography A*, May 2013, vol. 1291, pp. 33-40.

Vagenende et al, "Allantoin as a solid phase adsorbent for removing endotoxins" Journal of Chromatography A, 1310 (2013), pp. 15-20.

Gagnon, P., Purification Tools for Monoclonal Antibodies, 1996, Validated Biosystems, Tucson; Morais, V., et al, Biotechnol. Appl. Biochem., 59 (2012) 50-54.

\* cited by examiner

METHOD OF PURIFYING AN ANTIBODY

CROSS-REFERENCE TO RELATED APPLICATIONS

This application is the U.S. National Stage of PCT/SG2015/050023, filed Feb. 17, 2015, which in turn claims the priority of U.S. provisional patent application No. 61/941,911 filed Feb. 19, 2014, the disclosure of which are incorporated herein by reference in their entireties.

BACKGROUND

Embodiments disclosed herein relate to methods for purifying antibodies, in particular IgG antibodies.

Anion exchange chromatography has been used for the purification of IgG antibodies because it selectively binds acidic contaminants, while IgG binds weakly, not at all, or it is repelled from the anion exchanger surface. This provides a convenient effective means of eliminating acidic contaminants from the antibody. Commonly practiced examples of anion exchange chromatography include bulk addition of positively charged polymers or particles to an IgG-containing sample, passage of the sample through a column packed with anion exchange particles in flow-through or void exclusion mode, or the technique of high performance tangential flow filtration in which the passage of antibody through membrane pores is prevented at very low salt concentrations exclusively by their electrostatic repulsion from positively charged groups on the surface of the membrane. With the exception of anion exchange on particle-packed columns operated in void exclusion mode (R. Nian et al, J. Chromatogr. A 1282 (2013) 127-132), all anion exchange methods require that the sample first be equilibrated to chemical conditions suitable for the binding of contaminants. This restricts the applicability of anion exchange because it means that a sample coming from a previous fractionation step must be buffer exchanged before being applied to an anion exchanger so that the conditions are appropriate for practicing the technique. The even more restrictive option is that the previous fractionation step itself must be selected so that the processed IgG is already provided under conditions suitable for application to an anion exchanger at the completion of that fractionation step. These restrictions particularly burden purification process sequences where an IgG antibody is resident in high salt conditions, such as following a cation exchange chromatography step, or multimodal (cation exchange-hydrophobic interaction, or hydroxyapatite step), or salt precipitation step, or where salt has been added to a sample for any reason.

Methods have been described for processing IgM-containing cell culture harvests that particularly remove chromatin catabolites (Gan et al J. Chromatogr. A, 1291 (2013) 33-40). These methods particularly describe the use of the DNA intercalating compound ethacridine for clarifying an IgG-containing cell culture harvest, under roughly physiological conditions.

Partial purification of monoclonal IgG antibodies by contaminant co-precipitation with caprylic acid (octanoic acid) has been disclosed (Chantuin, A., et al, Arch. Biochem. Biophys. 89 (1960) 218-220). The fatty acid binds to all proteins but selectively precipitates non-IgG contaminants (Gagnon, P., Purification Tools for Monoclonal Antibodies, 1996, Validated Biosystems, Tucson; Morais, V., et al, Biotechnol. Appl. Biochem., 59 (2012) 50-54). Process development guidelines for application to cell-free cell culture harvests have been indicated (Gagnon supra). Application of caprylic acid to cell-containing cell culture harvests has been described (Brodsky et al Biotechnol. Bioeng. 109 (2012) 2589-2598). The technique has the unfortunate feature of co-producing a turbid, sticky, electronegative haze that interferes with further purification (Gagnon supra; Brodsky et al supra).

Allantoin is an FDA-approved inflammatory agent used widely in over-the-counter healthcare products. It is known to remove endotoxin from protein solutions, including from solutions of IgG (V. Vagenende et al, ACS. Appl. Mater. Interfaces, 22 (2013) 4472-4478; V. Vagenende et al, J. Chromatogr. A 1310 (2013) 15-20).

SUMMARY

In certain aspects, the invention provides methods of purifying an IgG antibody from a preparation containing the antibody and contaminants, preferably where the preparation has been processed to remove at least 95% of the chromatin present in the original production medium from which it is derived. The method includes a step of contacting the preparation with an electropositive membrane having a porosity that retains at least 50% of non-adsorbed solutes with a hydrodynamic diameter greater than a selected size but permits passage of non-adsorbed solutes with a hydrodynamic diameter less than the selected size and the selected size may be any amount between about 10 nm and about 15 nm. During at least a portion of the contacting step the preparation comprises a salt such that (1) when the salt is present at a concentration less than about 50 mM, a pH value of the preparation is in a range from about 3 to within about 0.5 pH units of the isoelectric point of the most alkaline glycoform of the IgG antibody in the preparation; or (2) when the salt is present at concentration greater than about 50 mM, a pH value of the preparation is in a range from about 3 to about 9. The final operating condition of the contacting step is defined by either an absence of excess salt in the preparation or a non-zero salt concentration in the preparation of not greater than 20 mM, and a pH value in a range from about 5 to within about 0.5 pH units of the isoelectric point of the most alkaline glycoform of the IgG antibody.

In certain embodiments, the preparation is provided for the method in a form having a reduced level of chromatin such that the amount of chromatin in the preparation is less than about 5% of the amount of chromatin which had been present in the source sample from which the preparation was obtained. In certain aspects, the source sample is a cell culture harvest, tissue sample, or bodily fluid having a substantial amount of chromatin present and the source sample is subjected to one or more processes for clarification, purification or fractionation to obtain the preparation having less than about 5% of the chromatin of the source sample for use in a method of the invention.

DETAILED DESCRIPTION

With respect to certain aspects of the invention it has been discovered that surprising improvements in the level of purification of preparations containing IgG antibodies is achievable with the performance of a chromatin-directed clarification followed by a fractionation process employing charged membranes having a porosity sufficient to retain the antibodies. Thus in certain aspects the purification methods of the invention are directed to preparations containing IgG antibodies where the preparation has been obtained through a process or processes which resulted in the substantial reduction in the levels of chromatin in comparison with its original source. For example, in certain embodiments the original source sample providing the desired IgG antibody is cell culture harvest, bodily fluid or tissue sample and the original source sample is subjected to steps for substantial reduction of chromatin levels; in certain such embodiments the chromatin levels of the original source sample are reduced by over 95% such that the preparation provided for the methods of the invention has less than 5% of the chromatin originally present in the source sample. Levels of chromatin reduction may be assessed with reference to the levels in the original source sample and in the preparation provided in the methods of the invention. Levels of chromatin reduction may be assessed with reference to levels of histone proteins and/or levels of DNA. In certain embodiments, the chromatin levels in the preparation are reduced by at least 96%, 97%, 98%, 99%, or 99.9% of the levels of chromatin in the original source sample or medium from which the preparation was ultimately derived. In certain embodiments where multiple steps are taken in preparing the preparation the determination of the reduction of chromatin levels is made with respect to the amount in the original sample prior to all steps of preparation or purification as opposed to a comparison with the penultimate sample just prior to obtaining the preparation.

In certain aspects, the invention provides methods of purifying an IgG antibody from a preparation containing the antibody and contaminants. The method includes a step of contacting the preparation with an electropositive membrane having a porosity that retains at least 50% of non-adsorbed solutes with a hydrodynamic diameter greater than a selected size but permits passage of non-adsorbed solutes with a hydrodynamic diameter less than the selected size and the selected size may be any amount between about 10 nm and about 15 nm. During at least a portion of the contacting step the preparation comprises a salt such that (1) when the salt is present at a concentration less than about 50 mM, a pH value of the preparation is in a range from about 3 to within about 0.5 pH units of the isoelectric point of the most alkaline glycoform of the IgG antibody in the preparation; or (2) when the salt is present at concentration greater than about 50 mM, a pH value of the preparation is in a range from about 3 to about 9. The final operating condition of the contacting step is defined by either an absence of excess salt in the preparation or a non-zero salt concentration in the preparation of not greater than 20 mM, and a pH value in a range from about 5 to within about 0.5 pH units of the isoelectric point of the most alkaline glycoform of the IgG antibody.

In certain embodiments, the preparation is provided for the method in a form having a reduced level of chromatin such that the amount of chromatin in the preparation is less than about 5% of the amount of chromatin which had been present in the source sample from which the preparation was obtained. In certain aspects, the source sample is a cell culture harvest, tissue sample, or bodily fluid having a substantial amount of chromatin present and the source sample is subjected to one or more processes for clarification, purification or fractionation to obtain the preparation having less than about 5% of the chromatin of the source sample for use in a method of the invention.

In certain aspects, embodiments disclosed herein provide an electropositive membrane having a porosity chosen such that at least a minimum percentage of non-adsorbed solutes with a hydrodynamic diameter greater than a selected size are retained on the basis of size, but non-adsorbed solutes with a hydrodynamic diameter less than the selected size are permitted to pass through the membrane. In certain embodiments, the minimum percentage can be any amount between 50% and 100%; in certain such embodiments the minimum percentage is 50%, 60%, 70%, 80%, 90%, 95%, or 99%. In any of these embodiments, the selected size may be any amount between about 10 nm and 15 nm; in certain such embodiments the selected size may be approximately 10 nm, 11 nm, 12 nm, 13 nm, 14, nm, or 15 nm. In certain embodiments, the porosity of the electropositive membrane may be chosen so as to retain all or substantially all of the desired IgG antibody to be purified from the preparation.

In some aspects, embodiments of the invention provide methods as described herein where the electropositive membrane has a porosity that is characterized as having an average pore size of about 3 nm to about 6 nm. In certain such embodiments the average pore size of the electropositive membrane would be about 6 nm, or about 5 nm, or about 4 nm, or about 3 nm. In some aspects, embodiments of the invention provide methods as described herein where the electropositive membrane has a porosity that is characterized as having a maximum pore size of about 9 nm or less, or about 8 nm or less, or about 7 nm or less, or about 6 nm or less, or about 5 nm or less. The hydrodynamic diameter of IgG antibodies, as measured according to their longest dimension, tend to be approximately 10-15 nm with some variation dependent upon local conditions. Given the flexibility of antibodies and variation in their size, selection of a pore size to retain antibodies typically requires a pore size appreciably smaller than the hydrodynamic diameter of the antibody of interest. For example, a maximum pore size of approximately 9 nm might retain substantially all of the larger IgGs whereas some smaller or more flexible IgGs may require a smaller maximum pore size such as approximately 5 nm. Moreover, pore size in a membrane can be expected to have a distribution such that the average pore size is appreciably smaller than the maximum pore size. For example, a membrane with a maximum pore size of approximately 9 nm may have an average pore size of 6 nm; similarly, a membrane with a maximum pore size of approximately 5 nm may have an average pore size of 3 nm.

In some aspects, embodiments of the invention provide methods for which, during a portion of the contacting step other than when the final operating conditions apply, the conditions of the preparation are characterized either by an absence of salt or the presence of a salt at a non-zero concentration up to saturation. In certain of such embodiments, the salt is sodium chloride, potassium chloride, ammonium chloride, sodium bromide, potassium bromide, ammonium bromide, sodium acetate, potassium acetate, ammonium acetate, and combinations thereof. In certain embodiments, during or prior to portions of the contacting step, the preparation is exposed to certain salt concentrations as discussed further herein.

In certain embodiments, a buffer exchange is performed during a portion of the contacting step with the electropositive membrane. In certain such embodiments the electropositive membrane is housed in a tangential flow filtration apparatus and the IgG antibody is concentrated in the retentate of the tangential flow filtration apparatus during at least portions of the contacting step.

In some aspects, embodiments of the invention provide methods which include the additional step of obtaining the preparation from the original source sample by separating the preparation from at least 95% of the chromatin residing in the source sample. In certain of such embodiments, the source sample is a cell culture harvest, a bodily fluid, or a tissue extract or such a material which has been subjected to some purification or processing. In certain embodiments, the preparation is obtained from the source sample through a process including fractionation. In certain such embodiments, the fractionation follows incubation of the source sample or a sample derived therefrom with allantoin and caprylic acid. In certain such embodiments, the preparation comprises re-solubilized IgG from the fractionation process.

In some aspects, embodiments of the invention provide methods where the preparation contains one or more agents that inactivate viruses. In certain such embodiments, the virus inactivating agents may be any of ethacridine, methylene blue, chlorhexidine, benzalkonium chloride, tri(n-butyl)phosphate, and combinations thereof. In certain such embodiments, the virus inactivating agents are each present in concentrations of about 0.1% or less.

In some aspects, embodiments of the invention provide methods where the electropositive membrane has a plurality of positively charged nitrogen-containing moieties immobilized covalently to or within the structure of the membrane so that they are situated on the surface of the membrane which contacts the preparation. In certain such embodiments, the positively charged nitrogen-containing moieties are any of (1) primary amines, (2) secondary amines, (3) tertiary amines, (4) quaternary amines (5) polyamines, (6) imines, (7) N-heterocycles, (8) amino acids, (9) N-hydroxyamides, (10), arylamines, polymers thereof, and combinations thereof. In certain such embodiments, the positively charged nitrogen-containing moieties also bind metal ions. In certain such embodiments, the positively charged nitrogen-containing moieties may also include one or more hydrophobic moieties of alkyl or aryl composition.

In some aspects, embodiments of the invention provide methods where the positively charged nitrogen-containing moieties are selected from the group consisting of tris(2-aminoethyl)amine, diethylenetriamine, triethylenetriamine, tetraethylenepentamine, polypropylenimine tetramine, poly(amidoamine) (PAMAM) dendrimer, deferoxamine (desferioxamine), arginine, histidine, histamine, imidazole, and combinations thereof.

In some aspects, embodiments of the invention provide methods where the positively charged nitrogen-containing moieties are each as described in formula I:

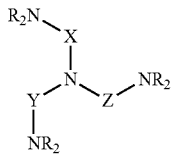

with each incidence of R as independently hydrogen or $C_1$-$C_{10}$ alkyl or $C_1$-$C_{10}$ alkyl substituted with hydroxyl, amino, or halo moieties, with the proviso that at least one of the R groups is the site of attachment to the electropositive membrane, optionally via a linker; and with each of X, Y, and Z is independently $(CH_2)_n$, where n is an integer from 2 to 8 and $CH_2$ groups may optionally be replaced by O, or NH. In certain such embodiments, the each incidence of R is independently hydrogen or $C_3$-$C_8$ alkyl, with the proviso that at least one of the R groups is the site of attachment to the electropositive membrane, optionally via a linker. In certain such embodiments, the each n is an integer from 2 to 6. In certain such embodiments, the positively charged nitrogen-containing tris(2-aminoethyl)amine.

In some aspects, embodiments of the invention provide methods which include the positively charged nitrogen-containing moieties are presented in a grafted dendrimeric form prepared by immobilizing a bivalent or trivalent primary amino compound on the membrane surface, then activating the free amino groups and attaching another layer of bivalent or trivalent amino compounds, and optionally repeating the process.

In some aspects, embodiments of the invention provide methods where the electropositive membrane is housed in a device to support tangential flow filtration and at least portions of the contacting step are conducted in tangential flow filtration mode. In certain such embodiments, the contacting step is performed through TFF using the electropositive membrane.

In some aspects, embodiments of the invention provide a kit for practicing any of the methods disclosed herein. In certain such embodiments, the kit also includes components for clarifying the source sample to obtain the preparation, such as clarifying components selected for reducing chromatin content.

With respect to certain aspects of the invention, it has been discovered that attempting anion exchange chromatography on a sample resident in a buffer that blocks the functionality of anion exchange chromatography, can be made useful by employing a positively charged membrane with pores of a size corresponding to a globular protein of 10-50 kDa, contacting the membrane with an antibody-containing solution resident in a high concentration of salt, then displacing the original solution with a second solution suitable for the practice of anion exchange chromatography. Without ascribing to any particular theory, the process is believed to work in the following: when a high salt sample, such as IgG in 1 M NaCl, is introduced to the membrane, IgG is retained but salts and contaminating species smaller than the pores flow through the membrane. These include small electroneutral, alkaline, and acidic contaminant, where the high salt has the particular effects of preventing retention of alkaline contaminants by electrostatic repulsion from the positively charged membrane, and preventing electrostatic binding of acidic contaminants to the positively charged membrane. This prevents the majority of acidic contaminants from fouling the positively charged surface, which is otherwise a general problem for anion exchange methods. Additional clean high-salt buffer fully washes small contaminants through the pores. The high-salt buffer is then replaced with a low- or no-salt buffer of neutral to mildly alkaline pH, and any remaining acidic contaminants large enough to be retained by the pores, such as virus particles if present, bind to the charged groups on the membrane. Since binding of small acidic contaminant was initially prevented by high salt and the small contaminants were eliminated by the pores, the full-charge capacity of the membrane is available for virus binding, in contrast to traditional anion exchange chromatography methods where the virus must compete with the acidic proteins for binding sites, with the result that its binding and removal is less efficient. Since retention of small alkaline contaminants was prevented by the high salt preventing their electrostatic repulsion from the membrane surface, this subpopulation of contaminants is also removed. No other anion exchange method provides this combination of performance features.

Advantageously, methods disclosed herein are not subject to volume limitations for samples that contain elevated salt concentrations. While conventional anion exchange methods can tolerate very large volumes, these can only be carried out when the salt concentration is low-to-nil. Thus, for example, in some embodiments the sample volume in methods disclosed herein can be substantially greater than the expressed volume of the membrane even at elevated salt concentration.

The disclosed methods also provide an additional opportunity associated with no other anion exchange method, that the sample can be washed with an intermediate buffer formulation designed expressly to dissociate contaminants that may initially bind to either the antibody or the membrane through non-specific chemical forces such as electrostatic interactions and hydrogen bonds, making it possible to eliminate the dissociated contaminants through the membrane pores. The following embodiment highlights the unique capabilities of the method: IgG is initially fractionated by precipitation in 2 M ammonium sulfate precipitation. The antibody precipitates, most contaminants are eliminated with the supernatant. The IgG is resolubilized by reducing the ammonium concentration to 1 M, for example by addition of water. This leaves the IgG needing additional purification, but since it resides in such a high-salt buffer it is incompatible with anion exchange chromatography, which would be the usual choice. One option would be to conduct a separate buffer exchange step, but this is costly and causes product to be lost. With the disclosed method, the high-salt sample is introduced into a tangential flow filtration apparatus equipped with electropositive membranes with an average pore size corresponding to a hypothetical globular protein of 50 kDa. IgG remains retained, but the high salt largely suspends electrostatic interactions as described above and permits the elimination of small contaminants without respect to charge. The high-salt buffer is then displaced by a low salt buffer such as 50 mM Tris, pH 8.2. Any remaining acidic contaminants bind to the electropositive membrane surface, but the IgG does not. The IgG may be concentrated, if desired, and collected for further processing, if desired.

In some aspects, embodiments disclosed herein relate to methods of purifying an IgG antibody resident in a solution with too high a salt concentration and/or pH value for subsequent purification by the traditional technique of anion exchange chromatography. This is achieved by contacting the solution with a positively charged (anion exchange) membrane with pores of a size corresponding to a globular protein of about 10-50 kDa, then exchanging the buffer to one suitable for practicing the method of anion exchange chromatography, whereupon remaining acidic contaminants will bind to the positively charged moieties on the membrane, with the effect of rendering a subsequent stand-alone anion exchange chromatography step unnecessary. In some embodiments, an intermediate step may be performed where the original solution is buffer exchanged into a buffer containing components intended to dissociate non-specific interactions between IgG contaminants, or between contaminants and the membrane, before the sample is buffer exchanged to conditions suitable for permitting acidic contaminants to bind to the positive charges on the membrane. In some embodiments, the original antibody-containing sample may be resident in a high concentration of salt as a result of having been previously fractionated by the technique of salt precipitation, or by having been eluted at high salt from a chromatography step, or by having had salt added.

In some aspects, embodiments disclosed herein relate to an IgG-containing cell culture harvest clarified by a method that particular removes chromatin, for example in one embodiment by contact with at least one fatty acid having 8 to 10 carbon atoms to form a mixture, contacting the mixture with one or more solids to form a mixture, wherein the one or more solids comprise a cationic functional group and a metal binding functional group, the metal binding functional group comprising a nitrogen-containing moiety selected from the group consisting of (1) a polyamine, (2) an imine, (3) an N-heterocycle, (4) an amino acid, (5) an N-hydroxyamide, (6), an arylamine, and combinations thereof, and separating solid materials after contacting the mixture with the one or more solids to provide a solution comprising the IgG antibody.

In some aspects, embodiments disclosed herein relate to methods for purifying an IgG antibody comprising a clarification method that particularly removes chromatin, followed by contacting the IgG-containing solution with a positively charged membrane with pores of a size corresponding with a hypothetical globular protein of about 50 kDa, and optionally exchanging the buffer to a formulation designed to weaken or suspend non-specific chemical interaction, then exchanging the buffer to a formulation generally considered suitable for performing the method of anion exchange chromatography in flow-through mode, after which the purified antibody is collected. The antibody may be further purified by other methods as desired.

In some aspects, embodiments disclosed herein relate to methods for purifying an IgG antibody comprising a clarification method that particularly removes chromatin, followed by a salt precipitation step, followed by contacting the high-salt IgG-containing solution with a positively charged membrane with pores of a size corresponding with a hypothetical globular protein of about 50 kDa, and then exchanging the buffer to a formulation suitable for performing the method of anion exchange chromatography in flow-through mode, after which the purified antibody is collected.

In some embodiments, the disclosed method surprisingly enables purification of therapeutic grade antibody from a process consisting of a clarification method that particularly removes chromatin, followed by the disclosed method where either salt is added to the sample before it is contacted with the positively charged membrane, or the original sample is buffer exchanged into high salt during an intermediate step prior to the buffer being finally exchanged into a buffer suitable for performing anion exchange chromatography. After completing the disclosed method, the sample may be processed by other methods, if necessary, to obtain the desired degree of purification.

In some embodiments, the disclosed method surprisingly enables purification of therapeutic grade antibody from a process consisting of a clarification method that particularly removes chromatin, followed by the method of salt-mediated IgG precipitation, with high-salt-containing resolubilized supernatant applied directly to the disclosed method. This core can be combined with virus inactivation, virus filtration, and ultrafiltration into final formulation to provide a total process with no requirement for any column chromatography steps, and particularly lacking a column chromatography step consisting of bioaffinity chromatography with immobilized protein A.

In some embodiments, the disclosed method surprisingly enables purification of therapeutic grade antibody from a process consisting of a clarification method that particularly removes chromatin, followed by a chromatography method in which the eluted IgG fraction exists in high salt, such as cation exchange chromatography, or multimodal chromatography employing a hydrophobic cation exchanger, or multimodal chromatography combining cation exchange and a metal affinity functionality, where the high-salt-containing IgG is applied directly to the disclosed method. This core can be combined with virus inactivation, virus filtration, and ultrafiltration into final formulation to provide a total process with no requirement for a column chromatography step consisting of bioaffinity chromatography with immobilized protein A.

In some embodiments, the disclosed method may be combined with an adjunct electropositive device to increase the efficacy of the purification process as whole. For example, instead of simply collecting the antibody at completion of the method, the antibody can be pumped through an adjunct anion exchange monolith, since mass transport in monoliths is more controlled and may support a higher degree of contaminant removal efficiency than the membrane. The monolith may be exchanged for any other type of device that may enhance the overall result, for example a membrane device with a different immobilized electropositive species, or a column packed with positively charged particles.

In some embodiments, the positively charged groups on the membrane may include at least one nitrogen-containing compound. In some such embodiments, at least one nitrogen-containing compound may embody the ability to bind metal ions. In some such embodiments, at least one nitrogen-containing compound may be positively charged and may include one or more compounds from the group comprising TREN; diethylenetriamine, triethylenetetramine, tetraethylenepentamine, polypropylenimine tetramine, PAMAM dendrimer (ethylenediamine core), deferoxamine (desferioxamine), arginine, histidine, histamine, and imidazole, among others.

In one or more of the previous embodiments, the positively charged group on the membrane is a compound of formula I:

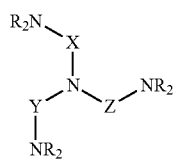

wherein each incidence of R is independently hydrogen or C1-C4 alkyl, with the proviso that at least one R is the site of attachment to a solid support, optionally via a linker; and each of X, Y, and Z are independently $(CH_2)n$, where n is an integer from 2 to 6, wherein a $CH_2$ group is optionally replaced by O, or NH. In one such embodiment, the metal binding functional group is the cationic chelating agent is tris(2-aminoethyl)amine, TREN. In other embodiments, any close TREN analogue, in accordance with formula I may be used in methods disclosed herein. Numerous commercially available compounds are encompassed by formula I and other synthetic designed compounds may be readily prepared by methods routinely used by those skilled in the art. For example, a tertiary amine of formula I may be prepared from a primary amine by sequential reductive amination reactions.

In one or more of the previous embodiments, a dendrimeric layer of positive charges is constructed on the membrane surface by successively activating the existing layer, for example by reductive amination, then introducing a multivalent amino species, washing away the unbound excess, then activating that surface again, etc. In the case of TREN for example, an initial layer of TREN is covalently attached to the membrane and the excess washed away. The bound TREN is then activated, the activation agent removed, and a fresh TREN introduced, with the effect of adding a TREN molecule on reactive amino groups at the termini of the originally immobilized TREN, with the effect of essentially doubling the depth of the charge field, and tripling the number of positively charged groups. After washing away unbound TREN, additional layers can be added.

In one exemplary embodiment using a membrane functionalized with TREN, TREN is covalently attached to the membrane by one terminal group, creating a species with 2 primary amine nitrogen atoms, 1 secondary amine nitrogen atom, 1 tertiary amine nitrogen, 5 terminal hydrogen atoms, and 3 hydrophobic ethyl groups. In another such embodiment, TREN is covalently attached to a solid by two terminal groups creating a species with 1 primary amine nitrogen atom, 2 secondary amine nitrogen atoms, 1 tertiary amine nitrogen atom, 4 terminal hydrogen atoms, and 3 ethyl groups. In another such embodiment, TREN is covalently attached to a solid by three terminal groups, creating a species with 3 secondary amine nitrogen atoms, 1 tertiary amine nitrogen atom, 3 terminal hydrogen atoms, and 3 ethyl groups. In one embodiment, covalently immobilized TREN may be present in any combination or subset of these or other forms.

In one or more previous embodiments where an electropositive species is immobilized on a membrane, species other than TREN may comprise one or more primary amines, one or more secondary amines, one or more tertiary amines, or one or more quaternary amines, with some specific examples including but not limited to 1,3-Diamino-2-propanol; 2-Amino-1,3-propandiol; Ethanolamine; 1-Amino-4-guanidobutane; Ammonia; 1,2-Diaminoethane; 1,3-Diaminopropane; 1,3-Diamino-2-propanol; bis(TRIS) pentane; 1,2-Diaminoethane; Trimethylamine; bis(3-Aminopropyl) amine; 4-Amino-4-(3-hydoxypropyl)-1,7-heptandiol; 1,3-Diaminopropane; 2-Amino-2-methyl-1,3-propanediol; 1,2-Diaminoethane; Diethanolamine; tris(Hydroxymethyl) aminomethane; N-(3-Aminopropyl) diethanolamine; Ethanolamine; N-Butylamine; 1,3-Diaminopentane; 2-(2-Aminoethoxy) ethanol; Polyethylenimine (MW: 2000); Polyallylamine, Polybenzallylamine, Polylysine, Polyarginine, 1-Amino-1-deoxy-d-sorbitol; tris(Hydroxymethyl) aminomethane; N,N-bis(2-hydroxyethyl) ethylendiamine; Pentaethylenhexamine; Triethanolamine; 1,3-Diamino-2,2-dimethylpropane; 3-Methylamino-1,2-propandiol; 2-Amino-ethanethiol; Diallylamine; Diethylentriamine; N-Methyldiethanolamine; 1,5-Diaminopentane; 4-Amino-4-(3-hydoxypropyl)-1,7-heptandiol; 1,4-Diaminobutane; Trimethylamine; Diethyltriamine; 6-Amino-1-hexanol; tris(Hydroxymethyl) aminomethane; 2-(Methylamino) ethanol; Methioninol; 4-Amino-1-butanol; and Hydrazine; or combinations thereof.

In one or more embodiments, positively charged species immobilized on a membrane may particularly embody a high degree of metal affinity may include but are not limited to Tris(2-aminoethyl)amine (TREN); TREN dendrimer, diethylenetriamine, triethylenetetramine, tetraethylenepentamine, polypropylenimine tetramine, PAMAM dendrimer (ethylenediamine core), deferoxamine, arginine, histidine, histamine, imidazole, aminoethyl phosphate, aminophenyl phosphate, or combinations thereof.

In one or more of the previous embodiments, the more than one species of positively charged species may be immobilized on the membrane. In one or more of the previous embodiments, positively charged species may be immobilized on the membrane in combination with species that are not positively charged. In one such embodiment, the additional species may confer enhanced ability to engage in hydrogen bonds, hydrophobic interactions, metal affinity interactions, van der Waals interactions, or electrostatic interactions with positively charged features of sample components. The inclusion of species other than positively charged species will not have the net effect of neutralizing the electropositivity of the membrane; the membrane will remain electropositive under the chosen application conditions regardless of the presence of immobilized species of differing chemical character. As a general matter, non-electropositive species may be immobilized on a membrane for the purpose of increasing the mass or diversity of contaminant components that may be removed by practicing the disclosed method.

In one or more of the previous embodiments, the pore size distribution of the membrane physically prevents the passage of a significant proportion of IgG, but allows for passage of dissolved species with a size corresponding to a hypothetical globular protein with a mass of 50 kDa, or a lower mass, down to 10 kDa or less.

In one or more of the previous embodiments, the base material of the membrane is a natural polymer such as cellulose, or a synthetic material such as polyethersulfone, polyamide, or other material suitable for synthesizing membranes.

In one of more of the previous embodiments, the physical configuration of the membrane is in the form of a flat sheet, or a spiral-wound sheet, or a hollow fiber, or other physical configuration.

In all of the previous embodiments, the conditions are unsuitable for the practice of anion exchange chromatography at some point during the contact of IgG containing solution with the positively charged membrane. Suitable conditions for anion exchange are generally understood to refer to conditions where the majority of contaminants bind and the majority of the IgG does not. For human, humanized, or chimeric IgG1, conditions considered suitable for practicing anion exchange would include low conductivity and a mildly acidic to mildly alkaline rang of pH. Conditions considered unsuitable for practicing anion exchange are understood to include conditions that unnecessarily prevent the binding of acidic contaminants, or unnecessarily cause the binding of IgG. For human, humanized, or chimeric IgG1, a salt concentration considered unsuitable for practicing anion exchange would have a conductivity higher than 1 mS/cm and potentially higher than 100 mS/cm, with any intermediate value, and with no upper limit. For such antibodies, a pH considered unsuitable for practicing anion exchange would be higher than about 0.5 pH units below its isoelectric point, or a pH lower than 1 unit below its isoelectric point. One of the particular benefits of the disclosed method is that neither salt concentration nor pH of the sample to be applied need be carefully selected nor even highly defined since the method tolerates conditions far beyond the usual limits for anion exchange as effectively as it tolerates conditions very close to conditions appropriate for anion exchange. One of the surprising features of the disclosed method is that it may benefit from conditions far outside the typical range for anion exchange chromatography because it permits the inclusion of additives to prevent electrostatic interactions, non-specific interactions, or even the inclusion of additives that enhance inactivation of viruses.

In one or more of the previous embodiments, the conditions of the original sample contacted with the positively charged membrane are unsuitable for practicing the method of anion exchange chromatography in its traditional modes of bind-elute, flow-through, or HPTFF.

In one or more of the previous embodiments, the conditions of the original sample contacted with the positively charged membrane are suitable for practicing the method of anion exchange chromatography in its traditional modes of bind-elute, flow-through, or HPTFF, but conditions are altered during the disclosed method to include salt concentrations and/or pH values unsuitable for practicing the method of anion exchange chromatography in its traditional modes.

In one of more of the previous embodiments, the conditions of the original sample contacted with the positively charged membrane are unsuitable for practicing the method of anion exchange chromatography in its traditional modes of bind-elute, flow-through, or HPTFF, and conditions are altered during the disclosed method to include alternative salt concentrations and/or pH values unsuitable for practicing the method of anion exchange chromatography in its traditional modes, before completing performance of the disclosed method by buffer exchanging to a formulation suitable for performing anion exchange chromatography in its traditional modes.

In one of more of the previous embodiments, the salt used to make the conditions unsuitable to practice the method of anion exchange is a so-called neutral salt such as sodium or potassium chloride.

In one of more of the previous embodiments, the salt used to make the conditions unsuitable to practice the method of anion exchange is a so-called chaotropic salt such as sodium or potassium thiocyanate, or guanidinium hydrochloride or acetate.

In one of more of the previous embodiments, the salt used to make the conditions unsuitable to practice the method of anion exchange is a so-called kosmotropic salt such as sodium or potassium sulfate, ammonium sulfate, potassium phosphate, sodium or potassium citrate.

In one of more of the previous embodiments, other additives may be included in either the original sample buffer, or an intermediate buffer, for the express purpose of dissociating non-specific interaction between contaminants and the antibody and/or between contaminants and the positively charged membrane. Such additives may include a nonionic chaotrope such as a ureide, for example urea or allantoin; or an organic solvent such as an alcohol or a glycol; or a sugar; or a surfactant such as a nonionic, zwitterionic, or cationic detergent.

In one of more of the previous embodiments, other additives may be included in either the original sample buffer, or an intermediate buffer for the express purpose of reducing virus content, such as a nonionic, zwitterionic, or cationic antiviral agent such as tri(n-butyl)phosphate, ethacridine, benzalkonium chloride, methylene blue, or chlorhexidine; urea or guanidine, a neutral or chaotropic salt.

In one of more of the previous embodiments, the conditions may be altered during an intermediate step for the express purpose of reducing virus, such as reducing the pH, or reducing the pH in conjunction with adding antiviral compounds, or in conjunction with adding compounds not themselves considered as major antiviral agents but nevertheless capable of enhancing the low-pH treatment, such compounds including sodium chloride, arginine, or argininyl compounds, or allantoin.

In one or more of the previous embodiments, the method is practiced in a device used to support tangential flow filtration. This is a system that permits retention and recycling of material that do not pass through the membranes, while materials that do pass through the membrane can be eliminated. This type of system also supports the technique of buffer exchange, which entails changing the buffer in which a protein is resident. In one such embodiment, the TFF unit may be fully automated. In certain of such embodiments, the process may be conducted manually, at any scale.

In one or more of the previous embodiments, the method may be practiced with so called-dead-end membranes, where the volume of the original high-salt samples is drawn down to a minimum, re-expanded with clean low-salt buffer, then drawn down again, etc. until it is judged that the buffer has been adequately exchanged to the low-salt formulation. This process may be conducted at any scale.

In one or more of the previous embodiments, the original sample containing the IgG is a bodily fluid, or harvest from a cell culture process, such as mammalian cells, yeast, bacteria, insect cells, or other biological production media.

In one or more of the previous embodiments, the IgG is an intact IgG with a molecular weight of about 150 to 170 kDa, of either monoclonal, or polyclonal, or recombinant, or synthetic, or enzymatic origin. In one or more such embodiments, the antibody may be bifunctional, referring to the ability of its respective antigen binding sites being immunospecific for different antigens. In one or more such embodiments, the antibody may be conjugated to a compound that endows the antibody with a functionality not usually associated with an antibody. In one or more of such embodiments, the added functionality may mediate a biological process in connection with therapy for a disease conditions; or the added compound may be fluorescent or colored, or generate a signal to aid detection of antigen-bearing substrates to which the antibody may be intended to bind.

In one or more of the previous embodiments, the sample contacted with the positively charged membrane consists of an IgG-containing cell culture harvest that has been clarified through application of a treatment that particularly reduces the chromatin content of the harvest. In one such embodiment, the chromatin-reducing treatment consists of contacting the harvest with positively charged particles. In one such embodiment, the chromatin-reducing treatment consists of contacting the harvest with positively charged membrane. In one such embodiment, the chromatin-reducing treatment consists of contacting the harvest with a positively charged hydrophobic compound, and that treatment may be combined with contacting the sample with a positively charged membrane or positively charged particles. In one such embodiment, the chromatin-reducing treatment may consist of contacting the harvest with a species of fatty acid, and that treatment may be combined with contacting the sample with a positively charged membrane or positively charged particles. In any of these embodiments, allantoin in a supersaturating amount may be added to the original harvest. In any of these embodiments, solids may be removed by centrifugation, membrane filtration, or depth filtration, including where the membrane or depth filter contains covalently immobilized positive charges.

In some embodiments, there are provided methods of purifying an IgG antibody from a preparation comprising contacting the preparation with an electropositive membrane having a porosity sufficient to retain at least 50% of the IgG antibody, wherein during contacting step the preparation comprises a neutral salt at concentrations up to saturation, and (1) when the neutral salt is present at concentration greater than about 50 mM, a pH value of the preparation is in a range from about 3 to about 9, or (2) when the neutral salt is present at a concentration less than about 50 mM, a pH value is in a range from about 3 to within about 0.5 pH units of the average isoelectric point of the IgG antibody.

Without being bound by theory, the high salt concentration of the initial contact solution may suppress electrostatic interactions and prevent the fouling of the membrane by the potentially large amount acidic contaminants in the initial contact solution, which are instead eliminated by passage through the pores in the membrane.

The relative volume of the preparation applied at the contacting step may be greater than about 50% of the expressed volumetric equivalent of the membrane. In methods disclosed herein, the relative volume can also be greater than 50%, 100%, 200%, 500%, 1000%, or more than the expressed volumetric equivalent of the electropositive membrane, theoretically without limit. The disclosed methods can also accommodate preparation volumes less than 50% of the expressed volumetric equivalent of the membrane, and still deliver all of the advantages it provides with larger volume samples. Thus, the sample volume may also be about 25% of the expressed volumetric equivalent of the membrane, or 10%, or 5%, or 1%, or a lesser non-zero volume.

Finally, methods disclosed herein further comprise adjusting operating conditions to the highest pH and lowest salt concentration that does not result in more than 5% of the IgG antibody being bound to the electropositive membrane. During this step acidic contaminants that have not been eliminated through the membrane pores bind to the positive charges and are thus removed from the IgG solution. Salt concentration and pH cannot be specified because they are different for each antibody. The cutoff can be not more than 5%, 4%, 3%, 2%, 1%, 0.5%, 0.1% or less, even approaching zero.

In some embodiments, methods further comprise equilibrating the electropositive membrane to any target salt concentration or pH prior to the contacting step. In some embodiments the methods further comprise not equilibrating the membrane prior to the contacting step.

In some embodiments, methods further comprise washing the electropositive membrane with a neutral salt at concentrations ranging from about 50 mM up to saturation after the contacting step. This step may enhance the ability of the method to eliminated small acidic contaminants through the pores of the membrane instead of them fouling (or consuming the capacity of) the positive charges on the membrane. In the event that the initial contact solution did not contain a high concentration of salt, this step provides the opportunity to liberate such contaminants that may have become bound to the positive charges and eliminate them through the pores in the membrane, leaving more capacity for the relative minority of acidic contaminants that may remain in the preparation.

In some embodiments, methods may further comprise concentrating the preparation at any step of the method after the contacting step.

In some embodiments, the neutral salt is selected from group consisting of sodium chloride, potassium chloride, ammonium chloride, sodium bromide, potassium bromide, ammonium bromide, sodium acetate, potassium acetate, ammonium acetate, and combinations thereof.

In some embodiments, prior to the contacting step the IgG preparation comprises one or more agents capable of disrupting non-specific interactions of the IgG antibody with contaminants, with the electropositive membrane, or with both.

In some embodiments, a solution during a washing step comprises one or more agents capable of disrupting non-specific interactions of the IgG antibody with contaminants, with the electropositive membrane, or with both.

In some embodiments, the one or more agents comprises a chaotropic salt selected from the group consisting of guanidinium hydrochloride, guanidinium acetate, sodium thiocyanate, potassium thiocyanate, and combinations thereof, wherein the chaotropic salt is present at a non-zero concentration up to about 1 M.

In some embodiments, the one or more agents comprises a non-ionic chaotrope.

In some embodiments, the non-ionic chaotrope is urea, wherein urea is present in a non-zero concentration up to about 6 M.

In some embodiments, the one or more agents comprises a nonionic, zwitterionic, or cationic surfactant.

In some embodiments, the one or more agents comprises an organic solvent selected from the group consisting of methanol, ethanol, isopropanol, and combinations thereof, wherein the organic solvent is present in a non-zero concentration up to about 10%.

In some embodiments, the one or more agents comprises an organic solvent selected from the group consisting of ethylene glycol, propylene glycol, dimethyl sulfoxide, and combinations thereof, wherein the organic solvent is present in a non-zero concentration up to about 25%.

In some embodiments, the one or more agents comprises a chelating agent selected from the group consisting of EDTA, EGTA, TREN, deferoxamine, and combinations thereof where the chelating agent is present in a non-zero concentration up to 50 mM.

In some embodiments, the one or more agents comprises non-ionic, zwitterionic, or cationic hydrophobic compounds.

In some embodiments, the one or more agents comprises one selected from the group consisting of ethacridine, methylene blue, chlorhexidine, benzalkonium chloride, tri(n-butyl)phosphate, and combinations thereof, wherein the one or more agents is present in a non-zero concentration up to about 0.1%.

In some embodiments, the one or more agents comprises a reducing agent.

In some embodiments, the reducing agent is selected from the group consisting of mercaptoethanol, dithiothreitol, dithioerythritol, glutathione, cysteine, and combinations thereof, wherein the reducing agent is present in a non-zero concentration up to about 20 mM.

In some embodiments, the preparation is a cell culture harvest clarified by a method that removes cells and debris.

In some embodiments, the preparation is a bodily fluid.

In some embodiments, the bodily fluid is a serum.

In some embodiments, the preparation is an eluate from a chromatography column.

In some embodiments, the preparation comprises re-solubilized IgG from a precipitation process.

In some embodiments, the electropositive membrane comprises a positively charged nitrogen-containing compound immobilized covalently to a surface of a membrane material.

In some embodiments, the positively charged nitrogen-containing compound comprises a moiety selected from the group consisting of (1) a primary amine, (2) a secondary amine, (3) a tertiary amine, (4) a quaternary amine (5) a polyamine, (6) an imine, (7) an N-heterocycle, (8) an amino acid, (9) an N-hydroxyamide, (10), an arylamine, polymers thereof, and combinations thereof.

In some embodiments, the positively charged nitrogen-containing compound further binds metal ions.

In some embodiments, the positively charged nitrogen-containing compound is selected from the group consisting of tris(2-aminoethyl)amine, diethylenetriamine, triethylenetriamine, tetraethylenepentamine, polypropylenimine tetramine, poly(amidoamine) (PAMAM) dendrimer, deferoxamine (desferioxamine), arginine, histidine, histamine, imidazole, and combinations thereof.

In some embodiments, the positively charged nitrogen-containing compound is a compound of formula I:

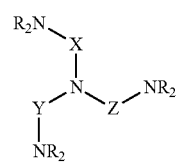

wherein each incidence of R is independently hydrogen or $C_1$-$C_4$ alkyl, with the proviso that at least one R is the site of attachment to a solid support, optionally via a linker; and each of X, Y, and Z are independently $(CH_2)_n$, where n is an integer from 2 to 6, wherein a $CH_2$ group is optionally replaced by O, or NH.

In some embodiments, the positively charged nitrogen-containing compound is tris(2-aminoethyl)amine.

In some embodiments, the positively charged nitrogen-containing compound is presented in a grafted dendrimeric form prepared by immobilizing a bivalent or trivalent primary amino compound on the membrane surface, then activating the free amino groups and attaching another layer of bivalent or trivalent amino compounds, and optionally repeating the process.

In some embodiments, the positively charged nitrogen-containing compound may include one or more hydrophobic moieties of alkyl or aryl composition.

In some embodiments, the electropositive membrane is housed in a device to support tangential flow filtration.

In some embodiments, there are provided kits for practicing the methods disclosed herein. Such kits may be suitable for performing small scale purification, or for conducting small scale experiments to determine specifications for large scale purification. There are other physical formats for carrying out method embodiments disclosed herein. One would be with a vertically- (or at least obliquely) mounted tangential flow (electropositive) membrane in a 50 mL (or smaller) centrifuge tube, where centrifugation provides the force to drive fluid through the membrane. Another might use an outlet-connected vacuum line. Another might be a closed unit with pressure fittings (threaded or luer-lock) on each end so that the unit could be fitted to a chromatograph.

In some embodiments, kits further comprise components for clarifying the preparation. In some such embodiments, clarifying components are selected for reducing chromatin content.

The following terms are defined so that the methods disclosed herein may be understood more readily. Additional definitions are set forth throughout the detailed description.

"TREN" refers to Tris(2-aminoethyl)amine. This electropositive compound is particularly known to embody strong affinity for metal ions. It may be chemically affixed to various materials to endow those materials with chemical characteristics mediated by TREN.

"Cell culture" refers to the cultivation of cells in a liquid medium, in the present context, for the purpose of producing IgG monoclonal antibodies. Cells employed for this purpose commonly include Chinese hamster ovary (CHO) cells, but may include cell types from other mammals, as well as non-mammalian animal cells, plants, and microbes. In all cases, the liquid medium contains nutrients to support cell growth.

"Harvest" or "cell culture harvest" generally refers to the contents of a bioreactor at termination of cell culture process. In addition to the IgG produced, the harvest will initially contain cells, cellular secretions, and expelled contents of dead cells, as well as the contents of the nutrient medium in which the cells were originally grown. These non-antibody components constitute the contaminants that are to be removed from the antibody. The particularly include host protein and DNA, but may also include virus and endotoxin. Cell culture harvests also frequently contain misassembled or damaged forms of antibodies in fragmentary forms.

"Clarified cell culture harvest" refers to a harvest from which the cells have been removed. Through the use of various additives, the clarification process may also have the ability to removal a significant subset of contaminants other than cells, in some cases having the particular ability to remove chromatin.

"Chromatin" refers to the genomic DNA expelled from the nucleus upon cell death, where the DNA remains associated with histone proteins in the form of nucleosome arrays, individual nucleosomes, degraded nucleosomes, and free DNA and histones, all of which may also occur in stable associations with antibodies and other cell culture harvest components.

"Tangential flow filtration (TFF)" refers to a method of membrane filtration in which fluid is forced through a space bounded by one or more porous membranes, where molecules small enough to pass through the pores are eliminated in the filtrate, and molecules large enough to be rejected by the pores remain in the retentate. The name tangential flow particularly refers to the fact that the direction of fluid flow is roughly parallel to the membrane, as opposed to so-called dead-end filtration where flow is roughly perpendicular to the membrane.

"Diafiltration" refers to a method of TFF wherein the pores are small enough to retain the product of interest but permit smaller materials to pass through. Continuous introduction of a solution of composition different from the original sample allows the composition to be changed gradually to the composition of the incoming solution, in a process sometimes referred to as buffer exchange.

"Protein" refers to any of a group of complex organic macromolecules that contain carbon, hydrogen, oxygen, nitrogen, and usually sulfur and are composed principally of one or more chains of amino acids linked by peptide bounds. The protein may be of natural or recombinant origin. Proteins may be modified with non-amino acid moieties such as through glycosylation, PEGylation, or conjugation with other chemical moieties. Examples of proteins include but are not limited to antibodies, clotting factors, enzymes, and peptide hormones.

"Host contaminant" or "Host cell contaminant" refers to biomolecules that are produced by the cells in which the product of interest is grown. The term may include various classes of host contaminants, such as host proteins and host DNA.

"Host protein" or "Host cell protein" or "HCP" refers to proteins that are produced by the cells in which the product of interest is grown. Such proteins represent one class of contaminants that are to be removed from the product of interest.

"Antibody" refers to an immunoglobulin of the class IgG, IgM, IgA, IgD, or IgE derived from human or other mammalian cell lines, including natural or genetically modified forms such as humanized, human, single-chain, chimeric, synthetic, recombinant, hybrid, mutated, grafted, and in vitro generated antibodies. The antibodies may be produced by a single clone, in which case they are referred to as monoclonal, or from more than one clone, in which case they are referred to as polyclonal. IgG antibodies particularly refer to a class of antibodies referred to as immunoglobulin G, which may also exist as one or a mixture of subclasses, for example in humans as $IgG_1$, $IgG_2$, $IgG_3$, or $IgG_4$; or in mice as $IgG_1$, $IgG_{2A}$, $IgG_{2B}$, or $IgG_3$; or in rat as $IgG_1$, $IgG_{2A}$, $IgG_{2B}$, $IgG_{2C}$. Antibodies produced naturally or recombinantly in eukaryotic hosts may exist in a variety of glycosylated forms, while antibodies produced in non-eukaryotic hosts may exist in a variety of glycosylated and non-glycosylated forms.

"Endotoxin" refers to a toxic heat-stable lipopolysaccharide substance present in the outer membrane of gram-negative bacteria that is released from the cell upon lysis. Endotoxins can be generally acidic due to their high content of phosphate and carboxyl residues, and can be highly hydrophobic due to the fatty acid content of the lipid-A region. Endotoxins can offer extensive opportunity for hydrogen bonding.

"Expressed volumetric equivalent" refers to an expression of anion exchange equivalency. The expression is understood to be arbitrary in some respect because the functional surface of many membranes are generally approximated as two-dimensional. However, their capacity can still be related to volumetric equivalents, typically based on comparison with porous particle anion exchangers where anion exchange interactions can take place in three dimensions due to the presence of the pores creating internally-accessible space within the body of the particles. This too is arbitrary since the degree of 3-dimensionality varies from one particle architecture to another. Some membranes also exist in formats that permit some degree of 3-dimensional access. Since the tradition in the field of anion exchange is to express capacity per unit volume, the concept has been carried over and applied to membranes, despite its imprecision. With lab-scale membranes, an expressed volumetric equivalent of an electropositive membrane may be given as mg of a selected protein or DNA per mL of membrane media. At industrial scale, the expressed volumetric equivalent may be expressed in mg or g per liter of membrane media.

"Polynucleotide" refers to a biopolymer composed of multiple nucleotide monomers covalently bonded in a chain. DNA (deoxyribonucleic acid) and RNA (ribonucleic acid) are examples of polynucleotides. Polynucleotides can have a high propensity for formation of hydrogen bonds.

"Protein preparation" refers to any aqueous or mostly aqueous solution containing a protein of interest, such as a cell-containing cell culture harvest, a (substantially) cell-free cell culture supernatant, or a solution containing the protein of interest from a stage of purification.

"Virus" or "virion" refers to an ultramicroscopic (roughly 20 to 300 nm in diameter), metabolically inert, infectious agent that replicates only within the cells of living hosts, mainly bacteria, plants, and animals: composed of an RNA or DNA core, a protein coat and, in more complex types, a surrounding envelope.

It will be useful to approach the practice of the disclosed methods with an awareness of its operating steps and options, and the effects they are expected to produce. These are illustrated by the following hypothetical example. A mammalian cell culture harvest containing an IgG monoclonal antibody to be purified, is clarified by a method that particularly reduces the content of chromatin in the harvest. Such clarification methods particularly reduce the content of large contaminating species in the harvest. The clarified harvest is introduced into a tangential flow filtration device equipped with a positively charged membrane suitable for practicing the disclosed method. Contaminants of a size small enough to pass through the pores are thereby eliminated, while the antibody is retained. The contaminant removal of this step can be enhanced by buffer exchanging the sample into a high salt buffer that suppresses attractive interactions between negatively charged contaminants and the positive charges on the membrane, and also suppresses repulsive interactions between positively charged contaminants and the positive charges on the membrane. One benefit of suppressing such interactions is that it prevents the charge capacity of the membrane from being consumed by fairly high concentrations of acidic contaminants in crude samples, and it thereby conserves the capacity of the membrane for binding small amounts of large acidic contaminants, such as virus or DNA, that may persist into the final stage of the method. Another benefit of suppressing such interactions is that it prevents highly electropositive contaminants from being retained by charge repulsion from the membrane, even though they may be small enough to pass through the pores. In addition to containing high salt concentrations, the buffer may optionally contain species of salts that tend to dissociate non-specific interactions between IgG and contaminants, or non-specific interactions between the membrane and contaminants. Other additives may be included to broaden the scope of the dissociative capability of the buffer, and/or a sequence of different dissociative buffers may be applied. Antibody is retained throughout this process by the porosity of the membrane. The high salt tolerance of the method highlights a valuable distinction of the disclosed method over all other forms of anion exchange chromatography except the column technique of void exclusion anion exchange chromatography. The membrane porosity and high salt tolerance of the method particularly highlights its benefits and distinctions over the membrane anion exchange method known as high performance tangential flow filtration (HPTFF). HPTFF fundamentally depends on electrostatic repulsion of the antibody from pores. An HPTFF feed stream must therefore be equilibrated to appropriately low conductivity and high pH conditions before the feed stream in introduced, and must be maintained within that range for the duration of the process. The final stage of the method is to buffer exchange the IgG to a predefined endpoint conditions representing the lowest conductivity and highest pH that does not result in the antibody being substantially bound to the positive charges on the membrane. At this point any acidic contaminants, large or small, but particularly including large contaminants such as DNA or virus will be bound to the positive charges on the membrane. It will be recognized that the earlier step of eliminating acidic contaminants small enough to pass through the membrane pores, will have maximized the capacity available to remove large acidic contaminants. This highlights another benefit and distinction of the disclosed method over traditional anion exchange methods, where removal of large acidic contaminants may be disadvantaged by smaller acidic contaminants competing for the same positive charges on the solid phase. Purified IgG is then removed from the unit.

A necessary step for practicing the method, until such time that positively charged membranes of appropriate pore size distribution become commercially available, will be to prepare the membranes from commercial media that have requisite porosity but lack positive charges. Chemical modification of the surfaces may be conveniently achieved by a variety of treatments, one of which is discussed here briefly for illustration purposes. A hydroxylated membrane is placed in a tangential flow filtration cassette and is equilibrated with 1 M NaOH under flow. 1 M NaOH, 1 mM sodium borohydride, 100 mM tris(2-aminoethyl) amine (TREN), and 100 mM epichlorohydrin, are then introduced and allowed to react for 4 h at 50 degrees C. with the buffer recirculating continuously through the membrane. The reaction solution can then be chased from the device and the membrane, now bearing TREN residues may be used to practice the disclosed method. Alternatively, if desired, the existing TREN groups may be further modified to increase the amount of positive charge on the surface. This can be accomplished by washing the membrane, still in the TFF unit, with 8% glutaraldehyde in 50 mM sodium phosphate, pH 6.4. The glutaraldehyde solution is then rinsed out with 50 mM phosphate pH, 6.4, followed immediately with 100 mM TREN in 50 mM boric acid, pH 9.1. The mixture is incubated for 2 hours then rinsed out with 50 mM phosphate, 1 M NaCl, pH 6.4, then with 20% ethanol. This process is understood to have immobilized second generation TREN molecules on the free amino termini of the first-generation immobilized TREN molecules, approximately doubling the total amount of charge on the membrane surface and extending it twice as far from the membrane surface. It will be apparent that the glutaraldehyde-TREN sequence can be repeated multiple times to increase the depth of the charged layer and thus the total number of charges per unit surface area of membrane. It will be apparent to the person of ordinary skill in the art that many alternative materials and chemical modification approaches can be used to prepare membranes suitable for practicing the methods disclosed herein, including, if desired, positively charged materials that also embody the potential to participate in secondary interactions such as hydrophobic, hydrogen bonding, metal affinity, pi-pi, or others.

A useful starting point in customizing methods disclosed herein to a particular monoclonal antibody preparation, such as exemplified by a cell culture harvest, is to clarify the feed stream by means of a treatment that particular includes positively charged materials, either solid or soluble, that form stable associations with the DNA component of chromatin, chromatin substructures such as nucleosomes, and histone-containing nucleosomal substructures. One such treatment may consist of simply combining the harvest with solids bearing positively charged surfaces. Another such treatment may consist of combining the harvest with positively charged polymers. A treatment described by Gan et al (supra) involves combining the harvest with allantoin and ethacridine, then adding positively charged particles and negatively charged particles to scavenge soluble non-antibody entities. An unpublished variant of that approach is to add methylene blue in place of ethacridine. Another unpublished variant involves the addition of a fatty acid in place of either the ethacridine or methylene blue. In all of these cases, solids may be removed by centrifugation and/or a filtration technique, where the filtration medium, in either a membrane or depth format, may bear positive charges. In all of the foregoing examples, the treated sample will be highly deficient in chromatin, which will render the sample composition especially suitable for practicing the disclosed method.

In some embodiments, it will be advisable to first define the lowest conductivity and highest pH that does not cause significant binding of the antibody to the positive charges on the membrane. A convenient starting point will be 50 mM Tris, pH 8.0. Subsequent experiments can evaluate lower and higher pH values, as well as lower buffer concentrations, or even the addition of salt, if necessary, such as NaCl, to prevent the IgG from binding to the positive charges. Once the pH and conductivity ranges of greatest utility are identified, it will be advisable as a general matter to run a 2-dimensional experiment where both those parameters are varied in order to define the combined conditions that support the most effective contaminant removal. The most effective conditions, when identified, will represent the target buffer exchange endpoint buffer for the final step of the disclosed method.

In some embodiments, it will be advisable to run a brief qualifying experiment in which NaCl sufficient to create a concentration of 1 M is added to a sample containing IgG, then the sample is processed by tangential flow buffer exchange, using the positively charged membrane, to the desired endpoint buffer, after which antibody recovery is measured. As a general matter, if the porosity of the original membrane was appropriate, antibody losses should be less than 5%.

In some embodiments, it will be advisable to include an elevated concentration of salt in the sample before introducing it to the TFF device housing the positively charged membrane to protect the membrane from the possibility of being fouled by contaminants residing within the sample.

In some embodiments, it will be advisable to apply an intermediate buffer for the express purpose of dissociating otherwise-stable associations between contaminating substances and the antibody, or between contaminating substances and the membrane, or both. Such intermediate buffer formulations may particularly include high concentrations of salt, including so-called chaotropic salts such as guanidinium chloride or sulfate, or sodium or potassium thiocyanate; urea; saccharides; surfactants; chelating agents; amino acids such as histidine or arginine, or other compounds as desired. A convenient formulation for performing a quick evaluation of the potential utility of this step is 50 mM Tris, 2 mM EDTA, 200 mM histidine, 2 M NaCl, pH 8.0.

In some embodiments, it may be expedient to practice the method on cell culture harvests that have been clarified by physical means only, such as centrifugation and/or membrane filtration, in which case the method can be used to create a high concentration of product early in the process, and a still-substantial reduction of contaminant content, though generally not the level of contaminant reduction that will be by practicing the method on cell culture harvests clarified by chromatin-directed methods or on partially purified materials.

The issues of flow rates, membrane surface areas, transmembrane pressures, volumes, and other basic operating parameters are well known from the field of tangential flow filtration and that practical knowledge may be applied directly without modification.

In some embodiments, it may be advantageous to conduct methods disclosed herein in which all of the disclosed elements are present, since the degree of influence asserted by the individual elements in the system as a whole cannot be predicted by their independent behavior. In practicing methods disclosed herein, single elements of the method may be serially excluded to provide a streamlined approach for any particular target IgG antibody. In some embodiments, statistical techniques such as Design of Experiments (DoE), as known in the art, may provide a means to identify a selection of a reduced number of method embodiments disclosed herein, designed to a particular IgG purification.

It will be apparent to the person of ordinary skill in the art that the method may be placed at any convenient point in a multi-step purification process, according to the needs of a particular process design or designer. As such, it may immediately follow cell culture clarification, it may be applied as the final fractionation step in a process, or it may be applied at any intermediate point in a process.

The following Examples are understood to be general, for illustration only, and should not be construed as limiting in any fashion.

EXAMPLES

Example 1

Preparation of electropositive membranes to practice the disclosed method. Electropositive membranes were prepared according to the method of van Reis as described in World Patent WO20018792 A2, FIG. 2A. In brief, 30 kDa cellulose membranes (Sartorius 14459-76-D) were reacted with 2 M 3-bromopropyl trimethyl ammonium bromide at room temperature overnight. Distinct from van Reis, the membrane was then washed 1 M NaCl, then water, to eliminate residual reactants and reaction byproducts Immobilization of quaternary amino groups was confirmed by binding of the anionic dye Methyl Blue.

Example 2

Application of an embodiment of the disclosed method. Mammalian cell culture harvest containing an IgG monoclonal antibody at a concentration of about 2.5 g/L was clarified by adjustment to pH 5.2, addition of 1% allantoin, followed by 0.4% sodium caprylic acid, then incubated stiffing for 2 hours. Solids were removed by microfiltration and the supernatant was flowed through a column containing agarose beads substituted with TREN (WorkBeads 40 TREN high, BioWorks, Uppsala), where the volume of the TREN column was 5% the volume of the original volume of cell culture harvest. This reduced host protein contaminants from the original 463,804 ppm to 8292 ppm. The sample was applied directly to a 30 kDa quaternary amine substituted filter and buffer exchanged to 50 mM Tris, pH 8.0. Host protein contaminants were reduced to 2414 ppm, representing a reduction of roughly 70%. By comparison, passage of sample through a Sartobind Q membrane adsorber (pore size 2-5 microns) in flow-through mode reduced host protein content only 29.5%. This shows that the effectiveness of the disclosed method is substantially greater than the industry standard practice of using electropositive solid phases (anion exchangers) in flow-through mode.

Example 3

Application of an embodiment of the disclosed method. Mammalian cell culture harvest containing an IgG monoclonal antibody at a concentration of about 0.6 g/L was clarified by adjustment to pH 5.4, addition of 1% allantoin, followed by 0.4% sodium caprylic acid, incubated 2 hours. Solids were removed by microfiltration and the supernatant was flowed through a column containing agarose beads substituted with TREN (WorkBeads 40 TREN high, BioWorks, Uppsala) where the volume of the TREN column was 5% the volume of the original volume of cell culture harvest then subsequently through a Sartorius PC1 depth filter. This reduced host protein contaminants from the original 3,841,397 ppm to 198 ppm. The sample was applied directly to a 30 kDa quaternary amine substituted filter and buffer exchanged to 50 mM Tris, pH 8.0. Host protein contaminants were reduced to 18 ppm. This example illustrates the ability of chromatin-directed clarification followed only by an embodiment of the disclosed membrane technique to achieve host contaminant levels below the level suggested by regulatory authorities for injectable therapeutic antibodies (100 ppm). It also highlights the unexpected ability of chromatin-directed clarification combined with the membrane fractionation method to obtain results better than are typically achieved with protein A affinity chromatography. Protein A is an appropriate reference standard because it is generally considered the most powerful antibody purification method available. IgG eluted from protein A columns typically contains 500-2000 ppm host cell proteins.

Example 4

Application of an embodiment of the disclosed method. Mammalian cell culture harvest containing an IgG monoclonal antibody at a concentration of about 1.5 g/L was clarified by adjustment to pH 5.4, addition of 1% allantoin, followed by 0.4% sodium caprylic acid, incubated stiffing for 2 hours. Solids were removed by microfiltration and the supernatant was flowed through a column containing agarose beads substituted with TREN (WorkBeads 40 TREN High, BioWorks, Uppsala), where the volume of the TREN column was 5% the volume of the original volume of cell culture harvest. This reduced host protein contaminants from the original 219,570 ppm to 4441 ppm. The sample was applied directly to a 30 kDa quaternary amine substituted filter and buffer exchanged to 50 mM Tris, pH 8.0. Host protein contaminants were reduced to 679 ppm. This example illustrates the ability of chromatin-directed clarification followed only by the disclosed filtration technique to achieve host contamination consistent with the levels produced by affinity chromatography with protein A.

Example 5

Integration of the disclosed method with an additional fractionation method. NaCl was added to the processed IgG from Example 4 to a final concentration of 1 M, and applied to a column of Capto adhere (GE Healthcare) equilibrated to 50 mM Tris, 1 M NaCl, pH 8.0. The Capto adhere column was eluted with a step to 50 mM MES, 300 mM NaCl, pH 6.0. HCP content of the eluted IgG was less than 1 ppm, and contained less than 1 ppm DNA, and less than 0.1% aggregates. This illustrates the ability of the disclosed method and a single polishing step to achieve or exceed the quality standards for therapeutic IgG by all three measures.

Example 6

Comparison of performance of charged versus uncharged membranes. The methods of Example 4 were repeated except using a 30 kDa cellulose membrane not modified to contain positively charged groups. Where the charged membrane reduced host protein contaminants to 679 ppm, the uncharged membrane reduced them only to 2280 ppm. However, the approximate 50% reduction of contaminant load highlights the point that contaminant reduction through the pores of the charged membrane eliminates a significant proportion of contaminants, and explains in part why the disclosed methods perform more effectively than the standard practice of using electropositive solid phases in flow-through mode (Example 2). Sample from the uncharged membrane was further fractionated by the method of Example 5. Where Capto adhere following the charged membrane reduced host protein to less than 1 ppm, Capto adhere after processing with the uncharged membrane reduced host protein to 86 ppm.

Example 7

Integration of the disclosed method with an additional fractionation method. Mammalian cell culture harvest containing an IgG monoclonal antibody at a concentration of about 2.5 g/L was clarified by adjustment to pH 5.2, addition of 1% allantoin, followed by 0.4% sodium caprylic acid, then incubated stiffing for 2 hours. TREN-bearing particles (WorkBeads 40 TREN High, BioWorks, Uppsala) were added at a ratio of 5% (v:v) and incubated stiffing for 4 hours, then centrifuged to remove solids. This reduced host protein contaminants from the original 243,997 ppm to 3551 ppm. The sample was titrated to pH 6.0 and diluted with 1:1 with water to reduce conductivity, then applied to POROS XS cation exchange chromatography media in a column, washed at pH 8.0, then eluted with a step to 50 mM NaCl. Host protein was reduced to 155 ppm. The sample was applied without equilibration to a quaternary amine membrane with a porosity of about 30 kDa. The sample was buffer exchanged into 50 mM Tris, pH 8.2, then removed from the system. Host protein was 24 ppm. Where Example 5 describes integration of the disclosed method with a follow-on polishing method, the present Example describes integration of the disclosed method with a previous antibody-capture method.

Example 8

Preparation of electropositive membranes to practice the disclosed method. Because appropriate membranes are not available to practice the method, they need to prepared. Regenerated cellulose membranes with an average pores size corresponding to a hypothetical globular protein of 30 kDa, were equilibrated with 1 M NaOH, 1 mM sodium borohydride, 100 mM tris(2-aminoethyl) amine (TREN), and 100 mM epichlorohydrin, then allowed to react for 4 h at 50 degrees C. with the buffer recirculating continuously through the membrane. The buffer was replaced with 1 M NaCl, then water, to wash away residual reactants and reaction byproducts Immobilization of TREN was confirmed by binding of the anionic dye Methyl Blue.

Example 9

Application of an embodiment of the disclosed method following chromatin-directed clarification of cell culture harvest. Mammalian cell culture harvest containing an IgG monoclonal antibody at a concentration of about 2.5 g/L was clarified by adjustment to pH 5.2, addition of 1 addition of 1% allantoin, followed by 0.4% sodium caprylate acid, incubated 2 h, add 5% BioWorks TREN, 4 hours incubation, centrifugation to remove solids, then passage through a depth filter (Sartorius PC1). This reduced host protein contaminants from the original 243,997 ppm to 236 ppm. The preparation was applied directly to a TREN-bearing cellulose membrane with a rated pore size corresponding with a globular protein with a mass of 30 kDa. The preparation was buffer exchanged into 50 mM Tris, 2 mM EDTA, 200 mM Histidine, 2 M NaCl, pH 8.0 to dissociate non-specific interactions, then buffer exchanged into 50 mM Tris, pH 8.2, then removed from the system. Host protein content of the IgG was reduced to 10 ppm.

Example 10

Application of an embodiment of the disclosed method following chromatin-directed clarification of cell culture harvest and IgG precipitation with ammonium sulfate. Mammalian cell culture harvest containing an IgG monoclonal antibody at a concentration of about 2.5 g/L was clarified by adjustment to pH 5.2, addition of 1% allantoin, followed by 0.4% sodium caprylate acid, incubated 2 h, add 5% BioWorks TREN, 4 hours incubation, then centrifugation to remove solids. This reduced host protein contaminants from the original 243,997 ppm to 3551 ppm. The IgG was precipitated with 2 M ammonium sulfate, then microfiltered to remove the supernatant. The IgG was resolubilized by adding 1 sample volume of water, leaving the IgG in 1 M ammonium sulfate. Host protein contamination was reduced to 1423 ppm. The sample was applied directly to a TREN membrane as described in Examples 8 and 10, then buffer exchanged into 50 mM Tris, 2 mM EDTA, 200 mM Histidine, 2 M NaCl, pH 8.0 to dissociate non-specific interactions, then buffer exchanged into 50 mM Tris, pH 8.2, then removed from the system. Host protein content of the IgG was reduced to 12 ppm.

Example 11

Application of an embodiment of the disclosed method following chromatin-directed clarification of cell culture harvest and cation exchange chromatography. Mammalian cell culture harvest containing an IgG monoclonal antibody at a concentration of about 2.5 g/L was clarified by adjustment to pH 5.2, addition of 1% allantoin, followed by 0.4% sodium caprylate acid, incubated 2 h, add 5% BioWorks TREN, 4 hours incubation, then centrifugation to remove solids. This reduced host protein contaminants from the original 243,997 ppm to 3551 ppm. The sample was titrated to pH 6.0 and diluted with 1:1 with water to reduce conductivity, then applied to POROS XS cation exchange chromatography media in a column, washed at pH 8.0, then eluted with a step to 50 mM NaCl. Host protein was reduced to 5 ppm. The sample was applied directly to a TREN membrane as described in Example 8, then diafiltered into 50 mM Tris, 2 mM EDTA, 200 mM Histidine, 2 M NaCl, pH 8.0 to dissociate non-specific interactions, then diafiltered into 50 mM Hepes, pH 8.2, then removed from the system. Host protein was reduced beneath the level of detectability.

Example 12

Production of TREN-dendrimer membranes. A membrane prepared as described in example 8 was washed with for 1 hour with 8% glutaraldehyde in 50 mM sodium phosphate, pH 6.4. The glutaraldehyde solution was rinsed out with 50 mM phosphate pH, 6.4, followed immediately with 100 mM TREN in 50 mM boric acid, pH 9.1. The mixture was incubated for 2 hours then rinsed out with 50 mM phosphate, 1 M NaCl, pH 6.4, then with 20% ethanol. This process is understood to have immobilized second generation TREN molecules on the free amino termini of the first-generation immobilized TREN molecules, doubling the total amount of charge on the membrane surface and extending it twice as far from the membrane surface. It will be apparent that the glutaraldehyde-TREN sequence can be repeated multiple times to further increase the effects.

All references cited herein are incorporated by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, chromatography conditions, and so forth used in the specification and claims are to be understood as being modified in all instances by the term "about" Accordingly, unless indicated to the contrary, the numerical parameters set forth in the specification and attached claims are approximations that may vary depending upon the desired performance sought to be obtained by the methods disclosed herein.

Many modifications and variations of the methods disclosed herein can be made without departing from their spirit and scope, as will be apparent to those skilled in the art. The specific embodiments described herein are offered by way of example only and are not meant to be limiting in any way. It is intended that the specification and examples be considered as exemplary only, with the true scope and spirit of the methods disclosed herein being indicated by the following claims.

What is claimed is:

1. A method of purifying an IgG antibody from a preparation comprising the antibody and contaminants, the method comprising:
    (a) contacting the preparation with a porous electropositive membrane comprising (i) a plurality of positively charged nitrogen-containing moieties, wherein the nitrogen-containing moieties comprise tris(2-aminoethyl)amine, and (ii) pores having a hydrodynamic diameter between about 10 nm and about 15 nm, or having an average hydrodynamic diameter of about 3 nm to about 6 nm, wherein during at least a portion of the contacting step the preparation comprises a salt at a concentration greater than about 50 mM and a pH from about 3 to about 9, and the electropositive membrane retains at least 60% of the antibody; and
    (b) performing a buffer exchange step comprising contacting the electropositive membrane after (a) with a solution comprising the salt at a concentration of 20 mM or less, and a pH in a range from about 5 to within about 0.5 pH units of the isoelectric point of a most alkaline glycoform of the IgG antibody.

2. The method of claim 1, wherein the pores have a pore size corresponding to a globular protein having a molecular weight of about 10 to 50 kDa.

3. The method of claim 1, wherein the electropositive membrane retains at least 99% of the antibody.

4. The method of claim 1, wherein the solution does not comprise a salt.

5. The method of claim 1, wherein the salt is selected from the group consisting of sodium chloride, potassium chloride, ammonium chloride, sodium bromide, potassium bromide, ammonium bromide, sodium acetate, potassium acetate, ammonium acetate, and combinations thereof.

6. The method of claim 1, wherein the method comprises the step of obtaining the preparation from a source sample by separating the preparation from at least 95% of chromatin residing in the source sample.

7. The method of claim 6, wherein the source sample is a cell culture harvest, a bodily fluid, or a tissue extract.

8. The method of claim 1, wherein the preparation is obtained from a source sample through a process comprising fractionation.

9. The method of claim 8 wherein the preparation comprises re-solubilized IgG from the fractionation process.

10. The method of claim 1, wherein the preparation contains one or more agents that inactivate viruses.

11. The method of claim 10, wherein the one or more agents that inactivate viruses are selected from the group consisting of ethacridine, methylene blue, chlorhexidine, benzalkonium chloride, and tri(n-butyl)phosphate.

12. The method of claim 10, wherein the one or more agents that inactivate viruses are each present in concentrations of about 0.1% or less.

13. The method of claim 1, wherein the plurality of positively charged nitrogen-containing moieties are immobilized covalently to or within the structure of the membrane and are situated on a preparation contacting surface of the membrane.

14. The method of claim 13, wherein the plurality of positively charged nitrogen-containing moieties are presented in a grafted dendrimeric form prepared by immobilizing a bivalent or trivalent primary amino compound on the membrane surface, then activating the free amino groups and attaching another layer of bivalent or trivalent amino compounds, and optionally repeating the process.

15. The method of claim 13, wherein the positively charged nitrogen-containing moieties comprise one or more hydrophobic moieties of alkyl or aryl composition.

16. The method of claim 1, wherein the plurality of positively charged nitrogen-containing moieties comprise one or more moieties selected from the group consisting of diethylenetriamine, triethylenetriamine, tetraethylenepentamine, polypropylenimine tetramine, poly(amidoamine) (PAMAM) dendrimer, deferoxamine (desferioxamine), arginine, histidine, histamine, imidazole, and combinations thereof.

17. The method of claim 1, wherein the electropositive membrane is housed in a device to support tangential flow filtration.

18. The method of claim 1, wherein the preparation comprises less than 5% of chromatin residing in a source sample from which the preparation was obtained.

* * * * *